(12) United States Patent
Lee et al.

(10) Patent No.: US 10,444,483 B2
(45) Date of Patent: Oct. 15, 2019

(54) METHOD FOR THREE-DIMENSIONAL IMAGING USING UPCONVERTING NANOPARTICLES

(71) Applicant: GWANGJU INSTITUTE OF SCIENCE AND TECHNOLOGY, Gwangju (KR)

(72) Inventors: Kang Taek Lee, Gwangju (KR); Yo Han Song, Gwangju (KR); Jin Ho Park, Gwangju (KR); Hong Li Jo, Gwangju (KR); Yeong Chang Goh, Gwangju (KR); Kyu Jin Shin, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 250 days.

(21) Appl. No.: 15/360,917

(22) Filed: Nov. 23, 2016

(65) Prior Publication Data

US 2017/0254996 A1 Sep. 7, 2017

(30) Foreign Application Priority Data

Mar. 3, 2016 (KR) ........................ 10-2016-0025389

(51) Int. Cl.
| | | |
|---|---|---|
| *G02B 21/00* | (2006.01) | |
| *H04N 13/204* | (2018.01) | |
| *G01N 21/64* | (2006.01) | |
| *G02B 21/36* | (2006.01) | |
| *H04N 5/33* | (2006.01) | |

(Continued)

(52) U.S. Cl.
CPC ..... *G02B 21/0076* (2013.01); *G01N 21/6428* (2013.01); *G01N 21/6458* (2013.01); *G02B 21/0032* (2013.01); *G02B 21/16* (2013.01); *G02B 21/361* (2013.01); *G02B 21/367* (2013.01); *G06T 7/521* (2017.01); *H04N 5/33* (2013.01); *H04N 13/204* (2018.05); *G02B 2207/114* (2013.01); *G06T 2207/10028* (2013.01); *G06T 2207/10061* (2013.01)

(58) Field of Classification Search
CPC .................................................. G02B 21/0076
See application file for complete search history.

(56) References Cited

U.S. PATENT DOCUMENTS

| | | | | |
|---|---|---|---|---|
| 2005/0230610 A1* | 10/2005 | Schreiber | ........... | G01N 21/6408 250/234 |
| 2014/0185284 A1* | 7/2014 | Hsu | .......... | F21V 9/08 362/231 |

OTHER PUBLICATIONS

[Supportive Materials for Exception to Loss of Novelty] Jo, Hong-Li et al, "Fast and background-free three-dimensional (3D) live-cell imaging with lanthanide-doped upconverting nanoparticles", Royal Society of Chemistry, Published on Oct. 25, 2015, Nanoscale, 2015, 7, pp. 19397-19402.

* cited by examiner

*Primary Examiner* — William C Vaughn, Jr.
*Assistant Examiner* — Daniel T Tekle
(74) *Attorney, Agent, or Firm* — Hauptman Ham, LLP (57) ABSTRACT

The present disclosure relates to a method for three-dimensional imaging, including introducing upconverting nanoparticles into a sample, illuminating near-infrared laser such that upconverting nanoparticles introduced into a sample is excited, detecting a visible ray emitted from the excited upconverting nanoparticles and capturing and acquiring two-dimensional images by scanning the sample in a depth direction of the sample, and generating a three-dimensional image of the sample using the two-dimensional images.

5 Claims, 10 Drawing Sheets

(51) Int. Cl.
*G02B 21/16* (2006.01)
*G06T 7/521* (2017.01)

METHOD FOR THREE-DIMENSIONAL IMAGING USING UPCONVERTING NANOPARTICLES

CROSS REFERENCE TO RELATED APPLICATION

This application claims the benefit of Korean Patent Application No. 10-2016-0025389, filed on Mar. 3, 2016, entitled "METHOD FOR THREE-DIMENSIONAL IMAGING USING UPCONVERTING NANOPARTICLES", which is hereby incorporated by reference in its entirety into this application.

BACKGROUND

1. Technical Field

The present disclosure relates to an imaging method, and more particularly, to an imaging method for acquiring a three-dimensional image of a sample such as a cell using upconverting nanoparticles.

2. Description of the Related Art

The fluorescence microscope is an optical system that is most widely used to observe biological cells. The fluorescence microscope acquires an image of a cell by making an enlarged cell image formed on an image sensor with fluorescent light emitted from a cell dyed with a fluorescent dye through an objective lens. A charge coupled device (CCD) is an implementation of the image sensor. The optical system of the fluorescence microscope has a conventional wide field microscope as a basic structure thereof. Thereby, not only fluorescent light emitted from the cell and light of the image formed on the CCD but also light which is unfocused and thus fails to form an image enters the image capturing device. Thus, it is difficult to acquire an accurate three-dimensional image of the cell. Due to this issue, contrast and resolution of the acquired three-dimensional image of the cell are degraded. In particular, for a fluorescence microscope employing a cell dyed with a fluorescent dye as a sample, the aforementioned issue is more serious than for a typical optical microscope, and it is difficult to correctly observe a fine structure of the cell.

To address this issue, a confocal laser scanning microscope has been introduced. The confocal laser scanning microscope overcomes the above issue by filtering out light fails to form an image, using a pin-hole as a spatial filter. Accordingly, the confocal laser scanning microscope has higher contrast and higher resolution than a typical wide field microscope. Further, the confocal laser scanning microscope can obtain an optically sectioned image of a cell. Such features of the confocal laser scanning microscope are essential conditions for constructing a three-dimensional image of a cell. Presently, the confocal laser scanning microscope implements a three-dimensional image of a cell with high contrast and high resolution, and thus has become an important indispensable cell imaging system in bioengineering research.

However, to create an image using a confocal laser scanning microscope, a laser beam scanning apparatus for scanning a sample with a laser beam is needed, and a system for regenerating an image from an optical signal reaching an optical detector through the pin-hole is also needed. Accordingly, the confocal laser scanning microscope inevitably uses x-y scanning technique in obtaining a sectioned image, and thus it takes a long time for the confocal laser scanning microscope to measure the three-dimensional image due to the limited speed of data acquisition. Thereby, it is difficult to observe change of the sample in real time using the confocal laser scanning microscope.

The description provided above is merely intended to provide further understanding of the present disclosure, and should not be understood as meaning that the present disclosure corresponds to a prior art technology which is well known to those skilled in the art.

SUMMARY

It is an aspect of the present disclosure to provide a method for three-dimensional imaging which provides the quality of an image captured by a confocal laser scanning microscope using upconverting nanoparticles (UCNPs), which are fluorescent particles, as probes and the imaging speed of the fluorescence microscope technology.

In accordance with one aspect of the present disclosure, a method for three-dimensional imaging includes introducing upconverting nanoparticles into a sample, illuminating near-infrared laser so that the upconverting nanoparticles introduced into the sample are excited, detecting a visible ray emitted from the excited upconverting nanoparticles and capturing and acquiring two-dimensional images by scanning the sample in a depth direction of the sample, and generating a three-dimensional image of the sample using the two-dimensional images.

A wavelength of the near-infrared laser may be between 900 nm and 1000 nm.

The near-infrared laser may be 980 nm continuous wave (CW) diode laser.

The acquiring of the two-dimensional images may include capturing images of the sample by moving an objective lens in the depth direction of the sample.

The generating of the three-dimensional image may include obtaining coordinates on x, y and z axes according to a peak point of a light emission signal of the upconverting nanoparticles.

The generating of the three-dimensional image may include measuring the peak point on a Gaussian distribution curve according to an intensity of the light emission signal of the upconverting nanoparticles for the two-dimensional images on the z axis, obtaining a coordinate on the z axis, measuring a peak point of a two-dimensional Gaussian distribution curve for the intensity of light emission signal for an image at the obtained coordinate on the z axis, and obtaining coordinates on the x and y axes and rendering the same.

The upconverting nanoparticles may be one selected from among ($NaYF_4:Yb^{3+}$, $Er^{3+}$), ($NaYF_4:Yb^{3+}$, $Tm^{3+}$), ($NaGdF_4:Yb^{3+}$, $Er^{3+}$), ($NaYF_4:Yb^{3+}$, $Er^{3+}/NaGdF_4$) and ($NaGdF_4:Yb^{3+}$, $Er^{3+}/NaGdF_4$).

A surface of the upconverting nanoparticles may be coated with a mixture of phospholipid-PEG and phospholipid PEG-amine.

According to embodiments of the present disclosure, a method for three-dimensional imaging has the following effects.

First, the imaging speed of a wide-field fluorescence microscope may be maintained, while temporal and spatial resolutions that the conventional confocal laser scanning microscope exhibits are maintained.

Second, since upconverting nanoparticles are used as imaging probes, and a source of light in the range of near-infrared rays is used for scanning, the efficiency of absorption of light by a biological tissue is relatively low, and thus high-resolution images may be obtained.

Third, since three-dimensional images may be provided in real time, the present disclosure may be effectively used in research on cell kinetics including nuclear absorption and single particle tracking.

DETAILED DESCRIPTION

Terms used in this specification are merely adopted to explain specific embodiments, and are not intended to limit the present disclosure. A singular expression includes a plural expression unless the two expressions are contextually different from each other. In this specification, a term "include" is intended to specify characteristics, regions, integers, steps, operations, constituents and/or components, and should be understood as not pre-excluding existence or addition of one or more other characteristics, regions, integers, steps, operations, constituents and/or groups.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Hereinafter, a method for three-dimensional imaging according to preferred embodiments of the present disclosure will be described with reference to the accompanying drawings.

If a two-dimensional image of a sample is acquired by scanning the sample in the depth direction using a wide-field fluorescence microscope, the fluorescence image may be blurred during scanning of the image. It is possible to obtain a clear image through complex mathematical reconstruction. However, optical stability may be lowered due to photoblinking of the imaging probe and photoleaching, and the image may be contaminated by autofluorescence.

In addition, in the conventional nanoparticle imaging, a source of visible light or infrared light is used. Accordingly, when a cell is imaged using nanoparticles, there is a high risk of damaging the cell, and autofluorescence of the cell may function as a significantly large background noise. In addition, in in vivo imaging, transmittance of visible light or infrared light through a biological body is very low.

Figure 1:
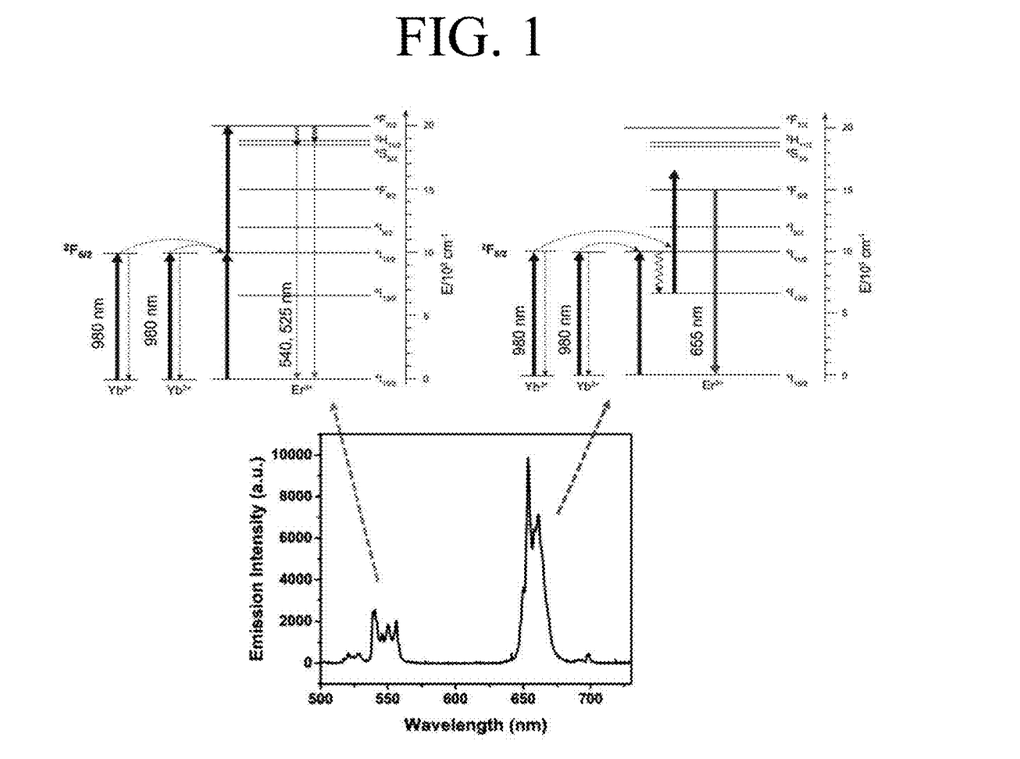
FIG. 1 illustrates paths of upconversion emission of NaYF4:Yb3+, Er3+ and an emission spectrum of upconverting nanoparticles whose surface is coated with a mixture of phospholipid-PEG and phospholipid of-PEG-amine.

The core configuration of the present disclosure for addressing the aforementioned issues is upconverting nanoparticles, which are used as a imaging probe. The upconverting nanoparticles absorb near-infrared (NIR) photons through optical upconversion, and emit visible photons or near-UV photons by nature. Thereby, a wavelength of a beam illuminated onto the sample is within the range of wavelength of NIR light, but the wavelength for imaging is within the range of wavelength of visible light. For example, the nanocrystal (NaYF4:Yb3+, Er3+), which is a material that is most widely used in research on upconverting nanoparticles, absorbs 980 nm photons, and emits visible photons through optical upconversion. FIG. 1 illustrates paths of upconversion emission of NaYF4:Yb3+, Er3+ and an emission spectrum of upconverting nanoparticles whose surface is coated with a mixture of phospholipid-PEG and phospholipid of-PEG-amine. As shown in the figure, NIR light is absorbed, and visible light is emitted through upconversion.

Since the upconverting nanoparticles are excited by NIR light, which is biologically friendly, and emit visible light. Accordingly, if the upconverting nanoparticles are used for cell imaging, they may rarely damage a cell specimen and autofluorescence may be prevented. Further, the converting nanoparticles may significantly increase transmittance through a biological body, and images may be obtained through a typical CCD for visible light, rather than through a CCD for NIR light. Accordingly, with the upconverting nanoparticles, consecutive images may be obtained for a long time since the upconverting nanoparticles do not cause photoblinking or photobleaching. Further, since the upconverting nanoparticles are a multipurpose nanomaterial capable of performing various biological functions through surface improvement, it may have universal and general biological applications.

The present disclosure employing the upconverting nanoparticles as a probe has the following features. According to an embodiment of the present disclosure, a method for three-dimensional imaging includes introducing upconverting nanoparticles into a sample, illuminating NIR laser to excite the upconverting nanoparticles introduced into the sample, detecting visible light emitted from the excited upconverting nanoparticles and acquiring two-dimensional images captured by performing scanning in the depth direction of the sample, and generating a three-dimensional image of the sample using the two-dimensional images.

First, a sample for three-dimensional imaging is prepared. Typically, various animal cells or vegetable cells may be used as the sample. The nanoparticles are introduced into the cell as an imaging probe. The upconverting nanoparticles used in the present disclosure are applicable to various embodiments in which the upconverting nanoparticles are excited by NIR light and emit visible light. For example, $(NaYF_4:Yb^{3+}, Er^{3+})$, $(NaYF_4:Yb^{3+}, Tm^{3+})$, $(NaGdF_4:Yb^{3+}, Er^{3+})$, $(NaYF_4:Yb^{3+}, Er^{3+}/NaGdF_4)$ and $(NaGdF_4:Yb^{3+}, Er^{3+}/NaGdF_4)$ may be used. The surfaces of these nanoparticles may be coated with a mixture of phospholipid-PEG and phospholipid-PEG-amine.

Figure 2:
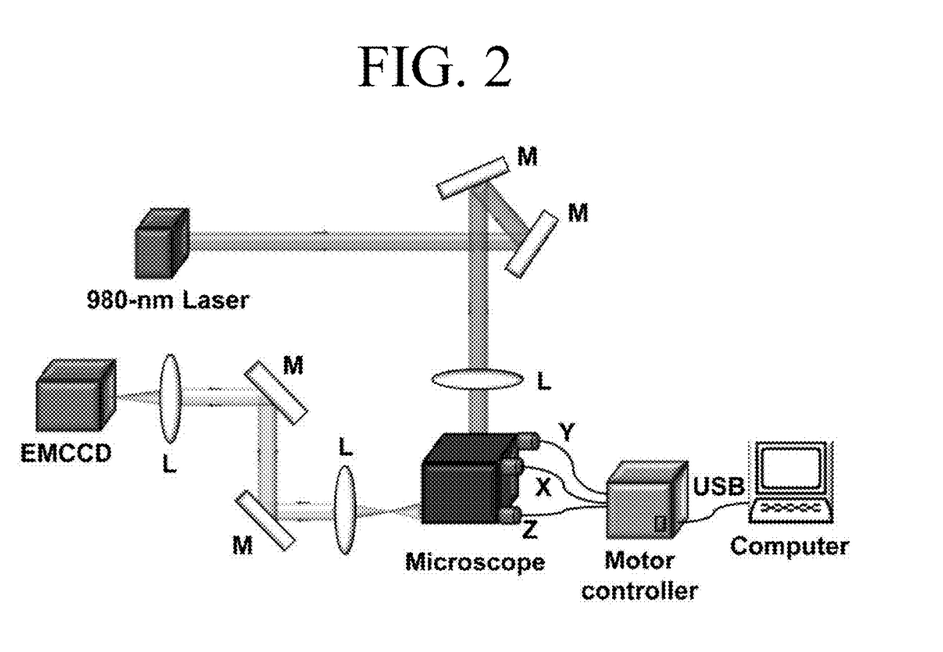
FIG. 2 is a schematic diagram illustrating a fluorescence microscope used for a method for three-dimensional imaging according to an embodiment of the present disclosure.

FIG. 2 is a schematic diagram illustrating a fluorescence microscope used for a method for three-dimensional imaging according to an embodiment of the present disclosure. Hereinafter, the procedure of capturing two-dimensional images will be described in detail with reference to FIG. 2. A prepared sample is positioned on a fluorescence microscope, NIR laser is illuminated onto the sample. The NIR laser serves to excite upconverting nanoparticles introduced into the sample, such that light having a wavelength in the range of visible light is emitted. The wavelength of the NIR light used for the separation ranges from 900 nm to 1000 nm. In particular, it is preferable to use laser of 980 nm wavelength in terms of absorption of the upconverting nanoparticles. In this case, any laser, whether it is Q-switching laser or femtosecond laser, may be used. Relatively low-cost continuous wave (CW) laser may be used.

A fluorescence image is acquired by detecting visible rays emitted from the upconverting nanoparticles excited by the NIR laser. Herein, the acquired image should be in the range of visible light rather than in the range of infrared light, and have a high signal sensitivity. Accordingly, an electron multiplying CCD (EMC CCD) may be used. In order to obtain the a three-dimensional image, a plurality of two-dimensional images of the sample ares acquired by scanning the sample in the depth direction ("z-direction"). Herein, the scanning refers to dividing the sample into parts in the depth direction and moving the sample or the objective lens such that the camera can capture multiple images of the sample. In this embodiment, two-dimensional images are captured, while the position of the objective lens is shifted in the depth direction of the sample through a motor controller attached to the microscope. Herein, the number and interval between the captured images are set by a computer connected to the motor controller. Typically, the number of captured two-dimensional images may be 15, and the distance between the images may be set to 500 nm. In this case, the range of scanning in the z-axis direction is about 7 μm, which corresponds to a range which allows measurement of sizes of almost all Hela cells. Herein, the exposure time of the EMCCD may be about 70 ms. Accordingly, it is possible to obtain two-dimensional images for building a three-dimensional image along the z-axis in about one second.

Figure 3:
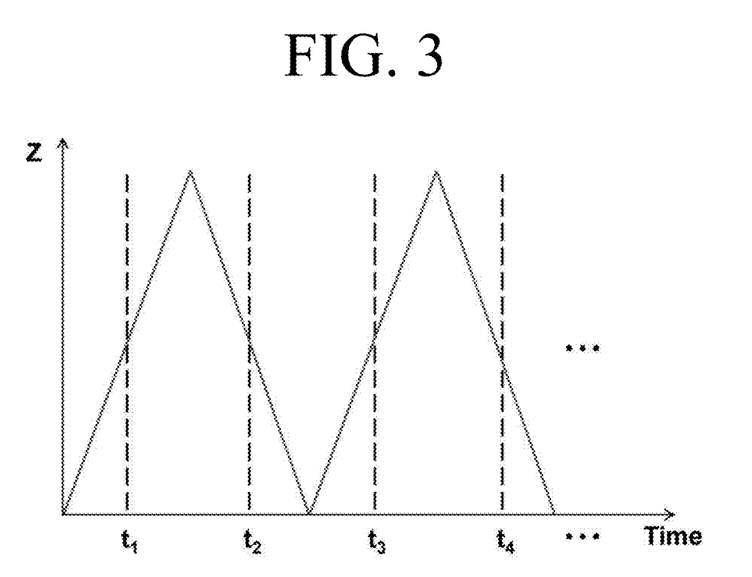
FIG. 3 is a graphic depicting the z-axis scanning position over time.
Figure 4:
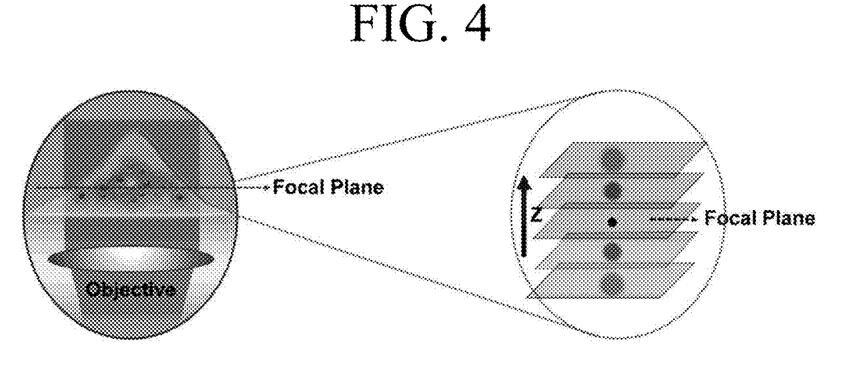
FIG. 4 schematically illustrates a procedure of obtaining two-dimensional images by performing scanning in the depth direction using a method for three-dimensional imaging according to an embodiment of the present disclosure.

FIG. 3 is a graphic depicting the z-axis scanning position over time. As shown in FIG. 3, the images may be consecutively obtained according to movement of the objective lens. In this case, the time interval between the images may be about one second. FIG. 4 schematically illustrates a procedure of obtaining two-dimensional images by performing scanning in the depth direction using a method for three-dimensional imaging according to an embodiment of the present disclosure. Multiple two-dimensional images (an image stack) may be obtained by scanning the sample in the z-axis direction by moving the objective lens. In the image stack, a plane in focus has a light emission point having the highest intensity, and the intensity gradually decreases in planes out of focus.

Figure 5:
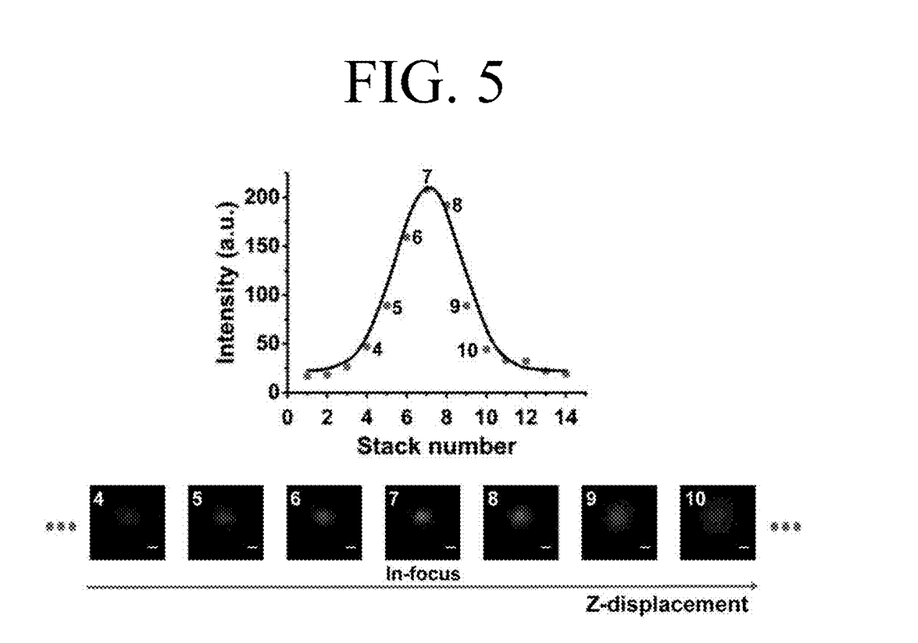
FIG. 5 illustrates the emission intensities and Gaussian distribution of upconverting nanoparticles along the z-axis.

Using the two-dimensional images obtained in this way, a three-dimensional image of the sample is generated. First, to correct the image stack along the z-axis, the position of a light emitting particle needs to be specified. FIG. 5 illustrates the emission intensities and Gaussian distribution of upconverting nanoparticles along the z-axis. As shown in FIG. 5, variation of the emission intensity of upconverting nanoparticles along the z-axis fits a Gaussian distribution. Accordingly, the peak point on the Gaussian distribution curve may be interpreted as the z-axis coordinate of a single upconverting nanoparticles.

Figure 6:
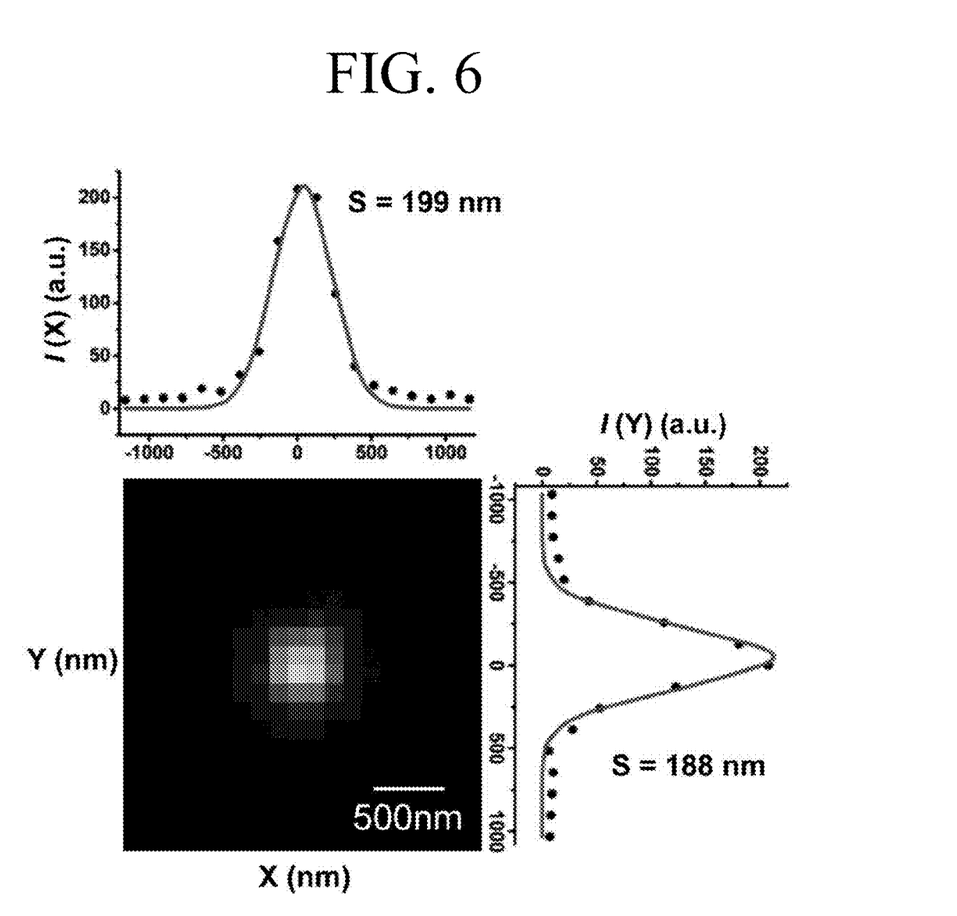
FIG. 6 illustrates the emission intensities and Gaussian distribution of upconverting nanoparticles in an x-y plane closest to a determined z-axis coordinate.

In addition, accurate coordinates in the x-y plane are needed to acquire a three-dimensional image. FIG. 6 illustrates the emission intensities and Gaussian distribution of upconverting nanoparticles in an x-y plane closest to a determined z-axis coordinate. Herein, "s" denotes a standard deviation of the Gaussian distribution. The x and y coordinates of the peak point of emission intensity are determined by the coordinates of the center in relation to the Gaussian distribution. Accordingly, a three-dimensional image may be generated by rendering point markers at the respective x, y, and z coordinates. The three-dimensional image may be generated by determining the three-dimensional center and repeating the rendering operation.

To obtain a three-dimensional image of a nanoparticle, accurate three-dimensional coordinates of the particle is needed. According to an embodiment of the present disclosure, in the Cartesian coordinate system, a z-axis coordinate is estimated first, and then two-dimensional coordinates on the x and y axes are estimated. Then, three-dimensional coordinates are estimated, and then a point is marked at the corresponding position to reconstruct the image. In this case, one set of 3-D imaging is possible at a time, and thus the change in position of the nanoparticle may be three-dimensionally tracked every one second.

An error for the position determined according to correction performed using the Gaussian distribution curve depends on the number of photons and the pixel size of the camera. The error range given by Equation 1, which was proposed by Thomson, is about 4 nm in the x-y plane and about 15 nm on the z axis. Accordingly, to more accurately determine the position, high-power laser is preferably used.

$$\Delta x \approx \sqrt{\frac{s^2 + a^2/12}{N}} \qquad \text{Equation 1}$$

N: the number of detected photons (=3000), s: the standard deviation of the Gaussian distribution (=~200 nm), a: the pixel size (=~500 nm)

A more detailed description of the present disclosure will be given below, based on an experimental example.

Figure 7:
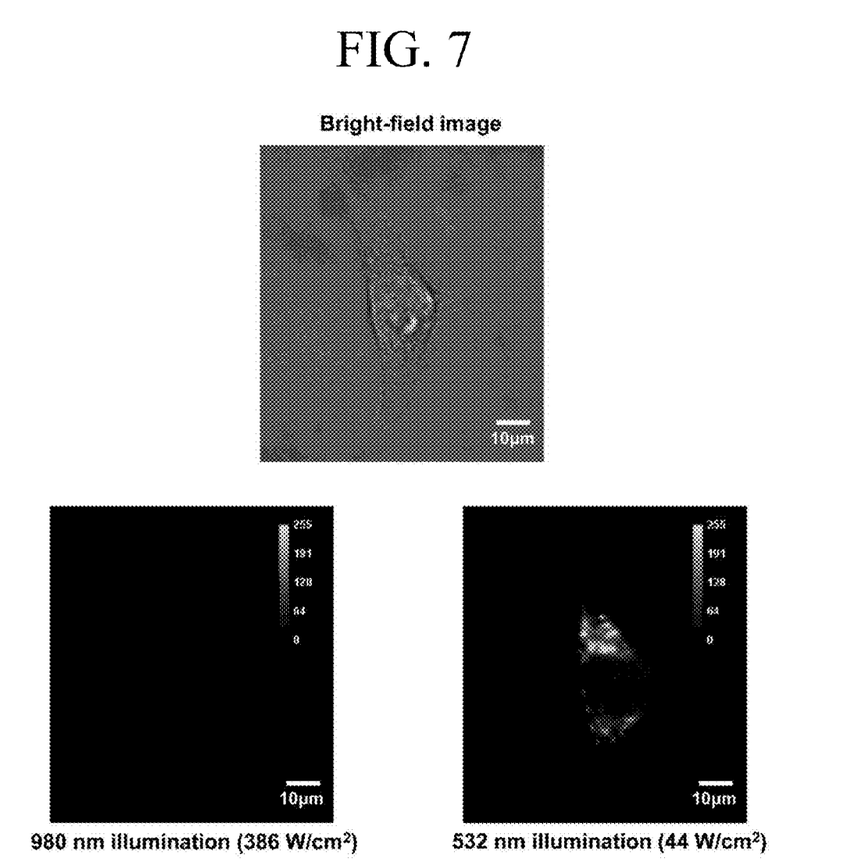
FIG. 7 shows images obtained by illuminating 980 nm laser and 532 nm laser onto a cell which does not contain a fluorophore.

To check if autofluorescence is created, 980 nm laser and 532 nm laser were illuminated onto a cell which did not contain a fluorophore (see FIG. 7). The powers used for the illumination were 386 W/cm$^2$ and 44 W/cm$^2$, respectively. As shown in FIG. 7, 980 nm laser did not cause autofluorescence even though the power thereof was 9 times greater than the power of 532 nm laser. On the other hand, 532 nm laser caused autofluorescence.

Figure 8:
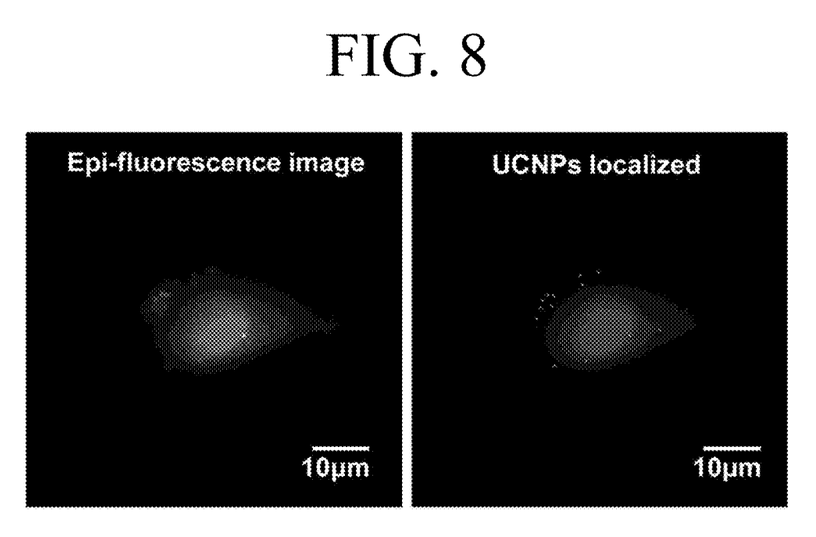
FIG. 8 illustrates comparison of images before and after determination of the position of upconverting nanoparticles.

The surface of hexagonal-(NaYF$_4$:Yb$^{3+}$, Er$^{3+}$), employed as upconverting nanoparticles, was coated with a mixture of phospholipid-PEG and phospholipid of-PEG-amine. The diameter of the upconverting nanoparticles was less than or equal to about 27.6 nm. The diameter obtained after coating was less than or equal to about 32.6 nm. A three-dimensional image of a fixed Hela cell was acquired before the upconverting nanoparticles were introduced into the cell. The cell was fixed in capturing the image thereof in order to check the effect of determination of a single three-dimensional particle (see FIG. 8). As expected, autofluorescence was not created, and it was seen that the blurring effect of the upconverting nanoparticles were eliminated by the position determination.

Figure 9:
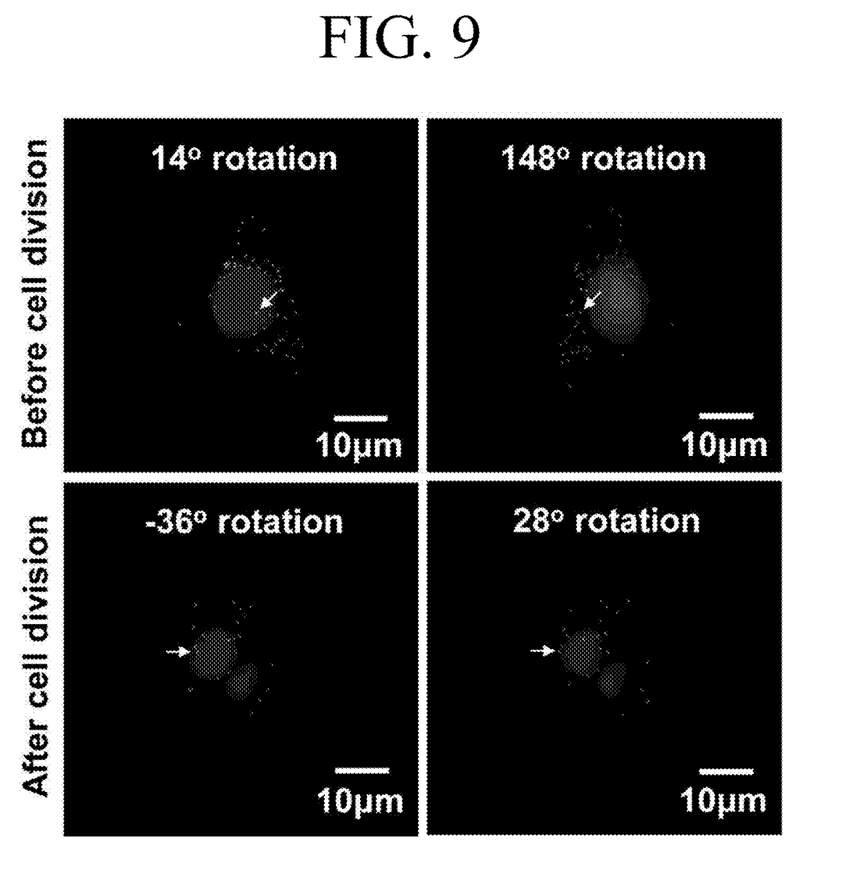
FIG. 9 shows and a three-dimensional image generated by injecting upconverting nanoparticles into a Hela cell and photographing the cell.

The method for three-dimensional imaging using upconverting nanoparticles according to the present disclosure may be the most appropriate model for visualizing the effect of introduction into the nucleus. To check if this is true, images of a live Hela cell are shown in FIG. 9.

Figure 10:
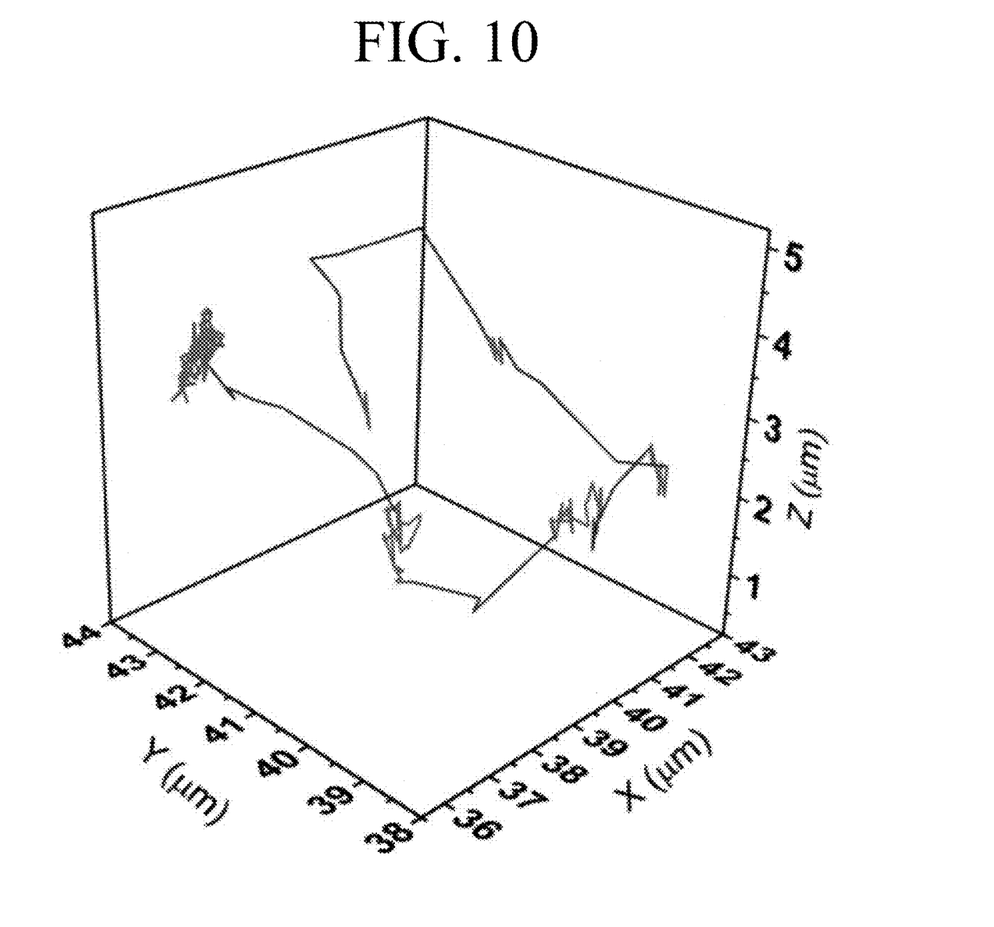
FIG. 10 shows a three-dimensional trajectory of a single upconverting nanoparticles, which is arbitrarily selected.

It is also possible to implement a three-dimensional image containing information about positions of all particles, including tracking of multiplexed single particles. FIG. 10 shows a three-dimensional trajectory of a single upconverting nanoparticles, which is arbitrarily selected. It is apparent that the trajectory is created by a few different transports. The area marked by blue indicates an active transport according to the cytoskeleton, and the area marked by red indicates limited diffusion.

Although the preferred embodiments of the present disclosure have been disclosed with reference to the accompanying drawings, those skilled in the art will appreciate that other embodiments may also be practiced without changing the spirit or essential features of the present disclosure.

Accordingly, the exemplary embodiments of the disclosure, as set forth above, should be construed in all aspects as illustrative and not limiting. It will be apparent to those skilled in the art that various modifications and variations can be made in the present disclosure without departing from the spirit or scope of the present disclosure. Thus, it is intended that the present disclosure covers the modifications and variations of this disclosure provided they come within the scope of the appended claims and their equivalents.

What is claimed is:

1. A method for three-dimensional imaging, comprising:
    introducing upconverting nanoparticles into a sample;
    illuminating near-infrared laser so that the upconverting nanoparticles introduced into the sample are excited;
    detecting a visible ray emitted from the excited upconverting nanoparticles while capturing and acquiring two-dimensional images by scanning the sample in a depth direction thereof; and
    generating a three-dimensional image of the sample using the two-dimensional images,
    wherein the generating of the three-dimensional image comprises:
        obtaining coordinates on x, y and z axes according to a peak point of a light emission signal of the upconverting nanoparticles,
    wherein the generating of the three-dimensional image comprises:
        measuring the peak point on a Gaussian distribution curve according to an intensity of the light emission signal of the upconverting nanoparticles for the two-dimensional images on the z axis;
        obtaining a coordinate on the z axis;
        measuring a peak point of a two-dimensional Gaussian distribution curve for the intensity of light emission signal for an image at the obtained coordinate on the z axis; and
        obtaining coordinates on the x and y axes and rendering the same, and
    wherein the upconverting nanoparticles are one selected from among ($NaYF_4:Yb^{3+}$, $Er^{3+}$), ($NaYF_4:Yb^{3+}$, $Tm^{3+}$), ($NaGdF_4:Yb^{3+}$, $Er^{3+}$), ($NaYF_4:Yb^{3+}$, $Er^{3+}$/$NaGdF_4$) and ($NaGdF_4:Yb^{3+}$, $Er^{3+}$/$NaGdF_4$).

2. The method according to claim 1, wherein a wavelength of the near-infrared laser is between 900 nm and 1000 nm.

3. The method according to claim 1, wherein the near-infrared laser is 980 nm continuous wave (CW) diode laser.

4. The method according to claim 1, wherein the acquiring of the two-dimensional images comprises:
    capturing images of the sample by moving an objective lens in the depth direction of the sample.

5. The method according to claim 1, wherein a surface of the upconverting nanoparticles are coated with a mixture of phospholipid-PEG and phospholipid PEG-amine.

* * * * *